United States Patent [19]

Clark et al.

[11] Patent Number: 5,259,835
[45] Date of Patent: Nov. 9, 1993

[54] WOUND CLOSURE MEANS AND METHOD USING FLOWABLE ADHESIVE

[75] Inventors: Jeffrey G. Clark, Raleigh, N.C.; Douglas M. Spranger; Paul J. Mulhauser, both of New York, N.Y.; Paul R. Lacotta, Oradell, N.J.

[73] Assignee: Tri-Point Medical L.P., Raleigh, N.C.

[21] Appl. No.: 752,019

[22] Filed: Aug. 29, 1991

[51] Int. Cl.⁵ .............. A61F 13/00; A61F 15/00; A61L 15/00
[52] U.S. Cl. .................. 602/48; 602/54; 602/58; 602/59; 606/213; 604/289; 604/310
[58] Field of Search ............ 602/48, 54, 55, 58, 602/59; 606/213, 214, 215, 216; 604/289, 310

[56] References Cited

U.S. PATENT DOCUMENTS

| | | | |
|---|---|---|---|
| 2,836,178 | 5/1958 | Barr | 602/59 |
| 3,528,426 | 9/1970 | Vukojevic | |
| 3,667,462 | 6/1972 | Moon | |
| 3,698,395 | 10/1972 | Hasson | |
| 3,995,641 | 12/1976 | Kronenthal et al. | |
| 4,161,176 | 7/1979 | Harris, II et al. | 602/58 |
| 4,210,148 | 7/1980 | Stivala | |
| 4,363,319 | 12/1982 | Altshuler | 604/304 |
| 4,646,731 | 3/1987 | Brower | 606/215 |
| 4,661,099 | 4/1987 | Von Bittera et al. | |
| 4,738,849 | 4/1988 | Sawyer | 604/304 |
| 4,753,231 | 6/1988 | Lang et al. | |
| 4,966,605 | 10/1990 | Thieler | 606/215 |
| 5,082,386 | 1/1992 | Hironaka et al. | 401/206 |

OTHER PUBLICATIONS

Leonard et al, A Spray Gun for Tissue Adhesive, May 1965, Surgery vol. 57, No. 5, pp. 749–750.

*Primary Examiner*—David Isabella
*Assistant Examiner*—Paul Prebilic
*Attorney, Agent, or Firm*—Oliff & Berridge

[57] ABSTRACT

A wound closure device employs a porous bonding member which receives a flowable adhesive capable of providing long term wound support. The bonding member is positioned by a carrier member that is used to achieve initial apposition of the wound and which may later be removed. An intermediate barrier may be provided between the bonding pad and the wound site. Alternatively, a rigid applicator may be utilized for positioning the bonding pad at the wound site. The closure device can include a supply of flowable adhesive for adhering the bonding member to the skin of the patient. Suitable flowable adhesives are cyanoacrylates. A form of packaging supports the wound closure member for preapplication of the adhesive and can serve as a part of a sterile barrier package.

57 Claims, 9 Drawing Sheets

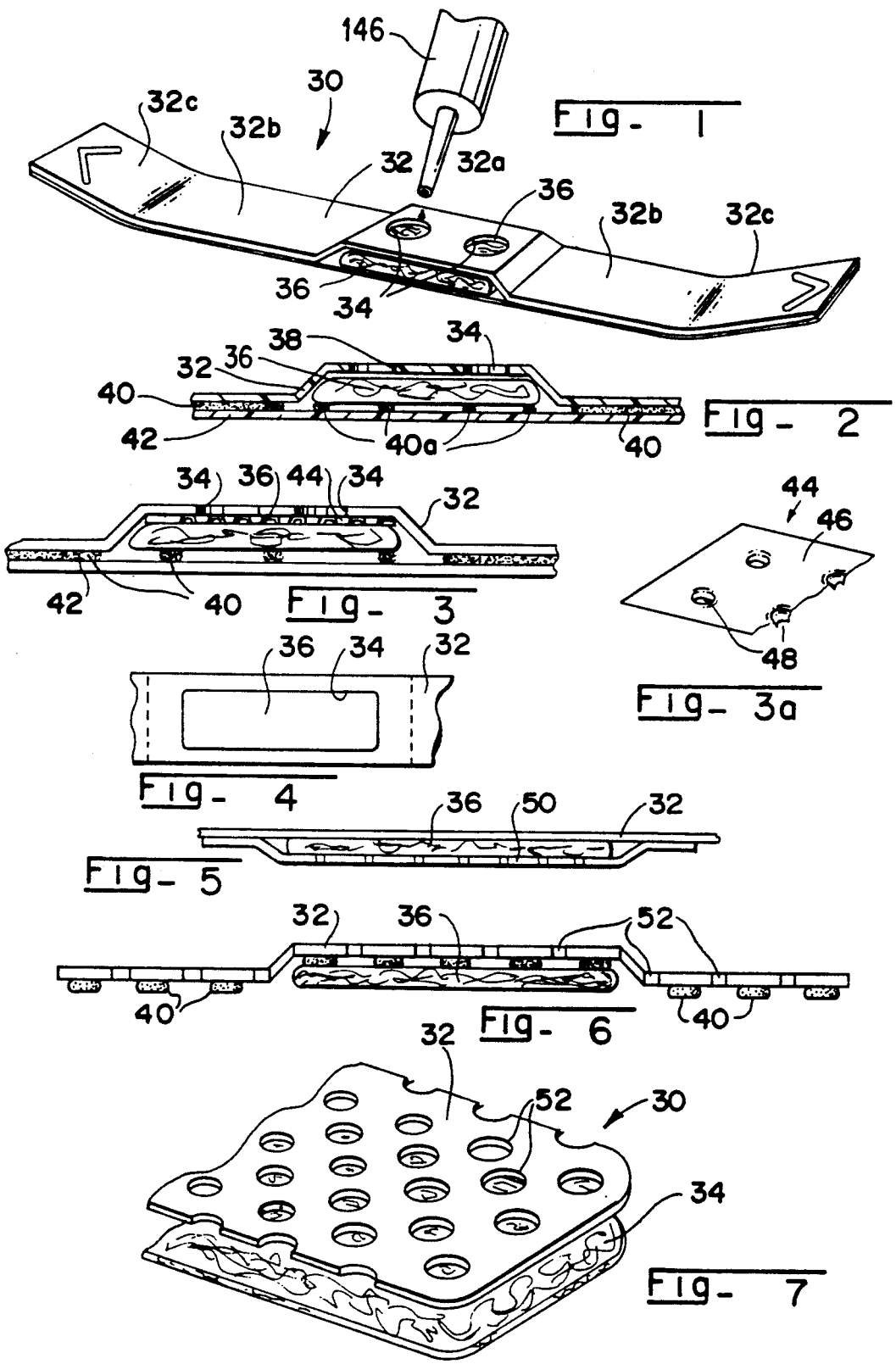

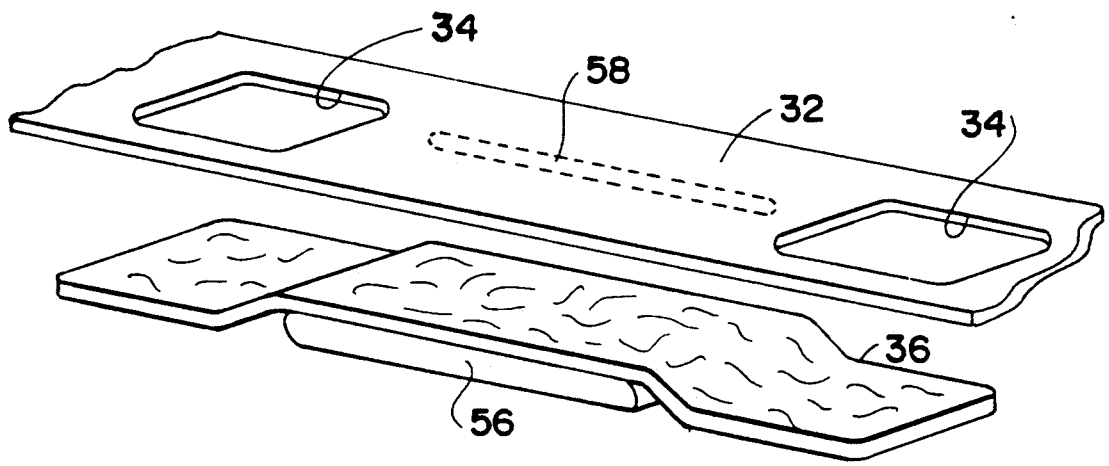
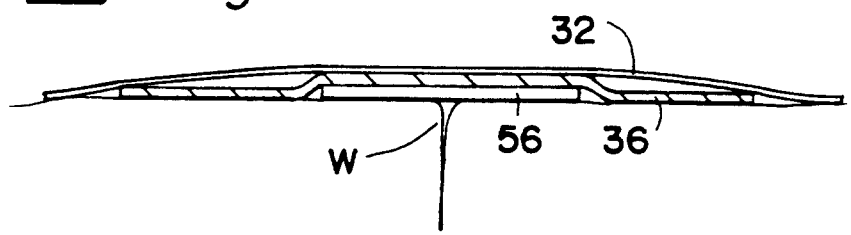
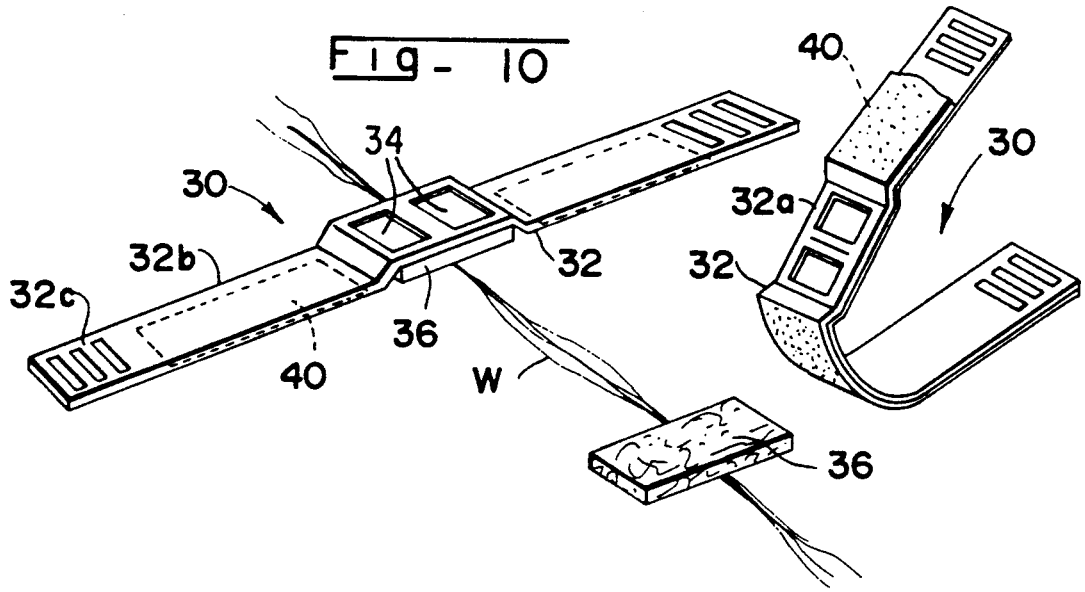

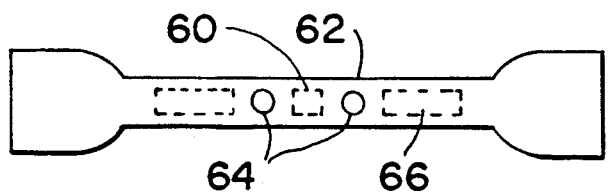
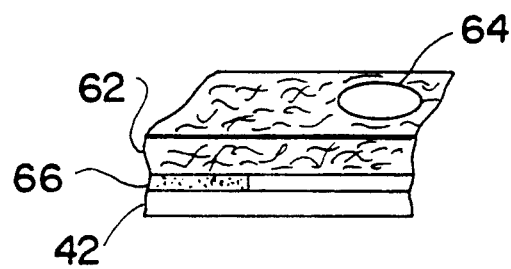
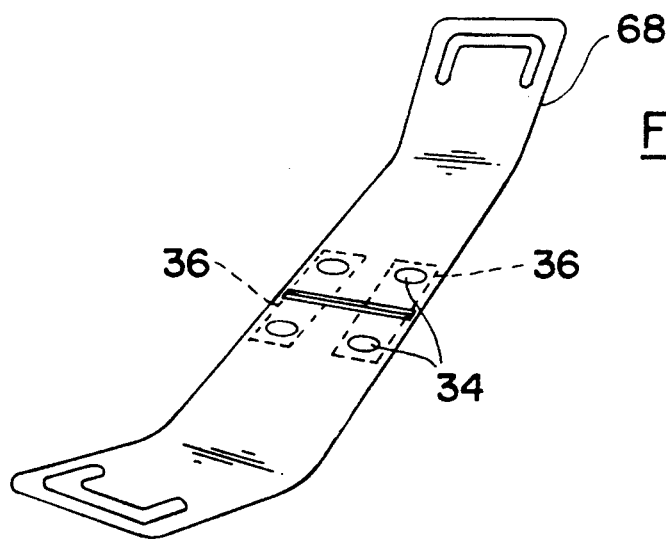

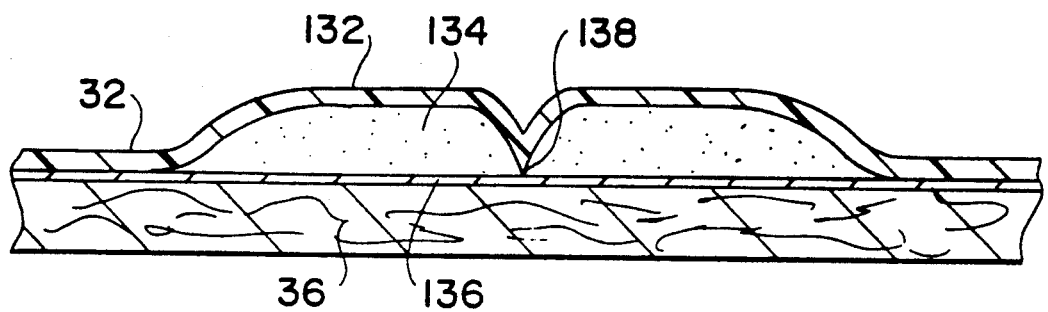
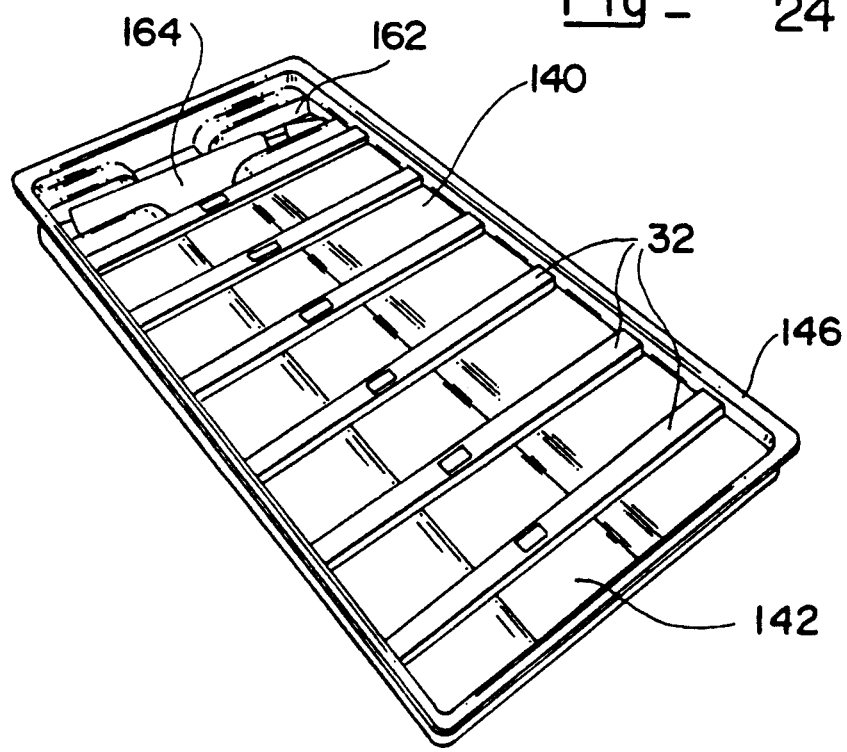

WOUND CLOSURE MEANS AND METHOD USING FLOWABLE ADHESIVE

FIELD OF THE INVENTION

This invention relates to medical and surgical wound apposition devices and methods. It relates specifically to adhesive skin closure members and methods.

BACKGROUND

There are currently in primary use three basic ways for closing wounds resulting from surgical incisions or accidental lacerations. These are sutures, surgical staples, and surgical skin tapes. Sutures are generally recognized as providing adequate wound support for the duration of wound healing. However, suturing involves additional trauma to the wound, as the needle and suture material must be passed through the tissue at the margins of the wound. In addition, suturing can cause cosmetically unattractive wound closure marks, can be time consuming, and, depending on techniques and types of sutures used, may require removal. Such removal entails further medical attention and can involve additional pain and trauma to the patient if the sutures become embedded in the wound.

Surgical staples have disadvantages similar to sutures in terms of cosmetic result. Further, removal of the staples can be painful and, depending on location and patient pain threshold, may require topical anesthetics.

Skin closure strips are utilized for closure of relatively superficial skin wounds. However, the contact adhesives that are used with such strips typically retain holding power for no more than a day or two and can lose holding power quickly in the presence of moisture, for example, perspiration.

Direct application of adhesives has also been proposed and used for wound closure purposes, especially involving cyanoacrylate adhesives. However, such materials have not achieved widespread use for wound closure.

SUMMARY OF THE INVENTION

The foregoing disadvantages of the above-described prior methods are overcome by placing a bonding pad over an apposed wound. A flowable, fast setting, high strength adhesive is introduced into the bonding pad or spaced bonding pads to bond the pad or pads to the skin at opposite wound margins. The bonding pad or an elongate carrier member for the bonding pad can include a skin contact adhesive useful for temporarily apposing the edges of the wound and holding the wound in apposed position until the adhesive introduced into the bonding pad has bonded the bonding pad to the skin of the patient. The bonding pad may be releasably secured to the carrier member so that the carrier member can be removed after the bonding pad has adhered to the skin. Multiple bonding pads may be mounted on a single carrier member. Means may be provided for preventing back flow of adhesive to a port through which the adhesive is introduced into the pad. A glue-impervious member may be positioned between the wound and the bonding pad to prevent adhesive from flowing into the wound.

The closure device may include a supply of adhesive for application to the bonding pad. The adhesive supply may be formed integrally with the carrier member.

Wound closure devices in accordance with the invention may be packaged for application of the adhesive into the bonding pad before use on a patient. The wound closure devices may be packaged in sterile form.

BRIEF DESCRIPTION OF THE DRAWINGS

FIG. 1 is a perspective view of a wound closure device in accordance with the invention;

FIG. 2 is a fragmentary sectional view of the wound closure device as shown in FIG. 1;

FIG. 3 is a fragmentary sectional view of a wound closure device employing an anti-back flow membrane;

FIG. 3a is a fragmentary perspective view of the anti-back flow membrane as shown in FIG. 3;

FIG. 4 is a partial plan view of a wound closure device in accordance with the invention having a single adhesive application port;

FIG. 5 is another embodiment of a wound closure device in accordance with the invention wherein a perforated membrane underlies the bonding pad;

FIG. 6 is another embodiment of a wound closure device having a perforated carrier member;

FIG. 7 is a fragmentary perspective view of another form of wound closure device having a perforated carrier member and a bonding pad coextensive with the carrier member;

FIG. 8 shows an embodiment of wound closure device employing a membrane for preventing adhesive from flowing to the wound;

FIG. 9 is a cross sectional view of the embodiment shown in FIG. 8 showing placement of the wound closure device over a wound;

FIG. 10 is a perspective illustration of wound closure devices in accordance with the invention showing initial placement of one wound closure device and subsequent removal of the carrier member of a second wound closure device;

FIG. 11 is a plan view of another embodiment of wound closure device formed of porous material and not requiring a carrier member;

FIG. 11a is a fragmentary perspective view of the embodiment of wound closure device shown in FIG. 11;

FIG. 12 is a perspective view of a carrier member having a plurality of bonding pads;

FIG. 23 is a partial cross sectional view of another arrangement employing a pierceable member for effecting supply of adhesive to the bonding pad;

FIG. 24 is a perspective view of a packaging arrangement for a plurality of closure devices in accordance with the invention;

DESCRIPTION OF THE PREFERRED EMBODIMENTS

Figure 13:
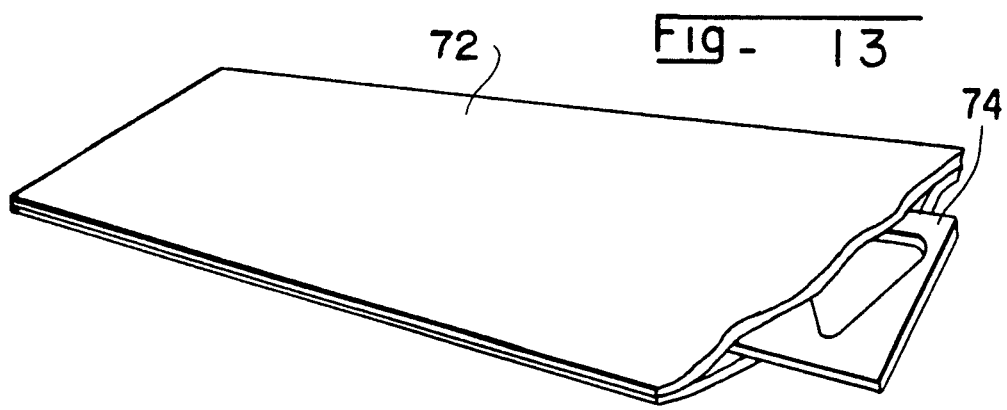
FIG. 13 shows a form of bonding pad having a stiffening element.

In FIG. 1, a first embodiment of wound closure device is illustrated. The closure devices disclosed have particular utility for closing skin wounds. In the closure device 30 as illustrated in FIG. 1, a carrier member 32 is provided. The carrier member may be formed of flexible, semi-rigid or rigid films of plastic material having sufficient strength in the longitudinal direction to maintain apposition of edges of a wound, as will hereinafter be described. For embodiments in which the carrier member is removed from the patient prior to wound healing, polyolefins are preferred materials for carrier members 32, as such materials have low affinities for known flowable, high strength adhesives, such as cyanoacrylates or epoxies, useable with the disclosed wound closure device. The carrier member 32 can include a central portion 32a, intermediate portions 32b and end portions 32c.

A bonding pad 36 is carried in the central portion 32a of the carrier member 32. The bonding pad is formed of a suitable porous structure or material into which an adhesive in a flowable form can flow and permeate or wet out all or portions of the pad, so that the pad forms a matrix for the adhesive, with the adhesive being present at the interface of the pad with the patient's skin. The bonding pad may be a knitted or woven mesh of, for example cellulosic fibers, or rayon acetate fibers, or other fibrous materials. The bonding pad 36 may also be formed of a nonwoven mesh of thermally or adhesively bonded fibers. Foams or combinations of fiber meshes with foams could be used for this purpose.

If, as will be described later, the carrier member is removed, the bonding pad 36 should have sufficient strength in the longitudinal direction to maintain apposition of a wound and for this purpose may include longitudinal reinforcement fibers. If the carrier member is to be removed, the bonding pad is secured by suitable means, such as a low bond strength adhesive 38, low strength heat sealing or other separable mounting means, to allow ready separation of the carrier member from the bonding pad, after the bonding pad has adhered to the skin, as will hereafter be described.

The central section 32a of the carrier member also includes an adhesive application port or ports, extending through the carrier member, for applying a flowable, high strength adhesive to the bonding pad 36. In the embodiment of FIG. 1, the carrier includes two ports 34, each of which can be disposed on one side or the other of a wound. Application of a flowable adhesive of appropriate viscosity to the bonding pad results in the adhesive flowing into the bonding pad and being applied against the skin surface underlying the bonding pad 36. Suitable high strength adhesives for this purpose are cyanoacrylate adhesives, which are especially useful because of relatively rapid bonding times and resistance to loss of adhesion from moisture. The alkyl family of cyanoacrylates, particularly higher homologue members, such as the butyl and octyl types, are believed to be especially useful because of long shelf life and good biocompatibility. Copolymers of cyanoacrylates and fast setting epoxies may also be useful The term "porous" is used in the specification and claims to mean materials or structures of the type as generally described above, into or about which liquid adhesive can flow and which serve as a matrix for the adhesive.

The wound closure device 30 includes means for holding the wound in apposed position and holding the bonding pad 36 in place during the time the adhesive bond between the bonding pad and the skin is being formed. In this regard, the intermediate portions 32b include a contact adhesive 40 on the underside thereof for at least temporarily holding the carrier member 32 onto the skin. Such contact adhesive may also be applied in a discontinuous fashion (indicated as portions 40a) to the skin contact side of the bonding pad 36 as shown in FIG. 2. The discontinuous application of contact adhesive to the bonding pad 36 is desirable so that portions of the bonding pad wetted with the flowable adhesive are in contact with and can form a bond with the skin. In order to protect the adhesive 40, a removable release layer 42a is applied to the underside of the carrier member 32 as shown in FIG. 2. Formulations for contact adhesives providing sufficient strength for wound apposition are known and no further description thereof is necessary.

The end portions 32c are free of contact adhesive and provide finger gripping tabs for facilitating placement or removal of the carrier member.

It is desirable to minimize the inadvertent deposition of the flowable adhesive on the patient or on instruments being used. For this purpose, it is desirable to employ an anti-back flow membrane 44 (FIG. 3), which draws the liquid adhesive into the bonding pad 36 and prevents excess adhesive from being present in the ports 34. For this purpose, membrane 44 in the form of a sheet 46 having a plurality of funnel-shaped apertures 48 (FIG. 3a) is useful. Such a membrane can be formed by application of a pin roller to a sheet of suitable plastic film, such as polyethylene, to form a screen. The screen 44 is interposed between the underneath side of the carrier member 32 and the bonding pad 36, as shown in FIG. 3. The funnel-shaped openings tend to draw the liquid adhesive in the direction of the bonding pad but tend to prevent reverse flow of adhesive back to the port.

The port for application of the flowable adhesive to the bonding pad 36 can be in the form of individual ports 34 as shown in FIGS. 1 and 2 or can be in the form of a single large port as shown in FIG. 4. Also, it is desirable to utilize a flowable adhesive having a color different from the bonding pad 36, so that application of the adhesive to the bonding pad 36 is visually evident.

In another arrangement shown in FIG. 5, a screen member in the form of a perforated plastic sheet 50 is located beneath the bonding pad 36. The sheet 50 can be heat sealed or adhesively attached to the bonding pad 36 or the underneath side of the carrier member 32 (as shown). In this arrangement, the plastic sheet is disposed between the bonding pad and the skin. Adhesion to the skin occurs as a result of adhesive passing through the perforations of the sheet 50. By controlling the amount of open area of the sheet 50, adhesion of the bonding pad to the skin can be controlled. The sheet 50 can also enable easier removal of the bonding pad 36, if necessary.

FIG. 6 shows another form of wound closure device wherein the carrier member 32 has a plurality of perforations 52. Such an arrangement can provide additional comfort to the wearer if the carrier member is retained in place during wound healing. Alternately, as shown in FIG. 7, the bonding pad material 36 may be coextensive with the perforated carrier member 32 thereby allowing increased area for adhesion. In this arrangement, the adhesive is applied through a plurality of perforations 52 in the carrier member to the bonding pad 54 so that an enhanced holding power can be achieved, substantially over a major portion of the length of the closure device 30.

Referring to FIGS. 8 and 9, a barrier layer 56 may be affixed by suitable means, such as a heat seal in the region 58 of the carrier member, which extends through to the barrier layer 56. The barrier layer 56 is of a suitable material, such as a plastic, which prevents flow of the adhesive directly onto to the wound site W. Instead, the adhesive is applied through longitudinally spaced ports 34 and adheres opposite end portions of the bonding pad 36 to portions of the wound margin which are spaced from the wound. In this manner, flow of adhesive into the wound is prevented.

FIG. 10 illustrates a typical wound closure technique using two wound closure devices in accordance with the invention. In the wound closure device 30 shown in the left hand portion of the drawing, the carrier member 32 has been applied across the wound W and is retained in place by the contact adhesive 40 applied to the intermediate portions 32b of the carrier member. The contact adhesive 40 has sufficient strength to hold the edges of wound W in apposition, with a bonding pad 36 extending across the wound margins. The end portions 32c are free of adhesive and can be gripped by the fingers to readily remove the carrier strip from the skin of the patient. While in this position, or previous to placement over the wound, a flowable adhesive is applied through the ports 34 of the carrier member to the bonding pad 36. After a predetermined time, usually about one minute, the adhesive, preferably a cyanoacrylate, has bonded the bonding pad 36 to opposite margins of the wound W. At this point, the carrier member 32 can be lifted at one end and removed, as shown in the right hand portion of the drawing. The bonding pad 36 is readily separable from the carrier strip 32, either by reason of having bond strength between the carrier and the bonding pad substantially less than the bond strength of the bonding pad to the patient's skin or by separable mounting arrangements (later described), so that the bonding pad 36 is left in place as the carrier member 32 is removed. The bonding pad 36 will remain in place until continued epithelialization loosens the adherence of the bonding pad to the skin or the bonding pad is deliberately removed.

As illustrated in FIG. 11, a wound closure device in accordance with the invention can be achieved without the use of a carrier member. In this case, the wound closure member comprises a length of porous, fibrous material formed in an elongate shape. The member 62 may have applied, on intermediate portions thereof, a contact adhesive 66, in the same manner as previously described. As shown in FIG. 11a, a protective release layer 42 is applied over the contact adhesive 66 and is removed just prior to application to the skin of the patient to achieve wound apposition. In this embodiment, markings or other graphics may be applied by suitable means, such as printing, to aid in proper placement of the flowable adhesive to the strip 62. As shown, such graphics can include a center mark 60 for guiding the centering of the strip 62 over the wound. Additionally, such graphics can include the adhesive application areas 64 for delineating correct adhesive placement. In this embodiment, the adhesive wicks through the porous sheet 62 and bonds the member 62 to the skin. In this arrangement, the material forming sheet 62 has sufficient tensile strength in the longitudinal direction to maintain wound apposition.

Referring to FIG. 12, a single carrier member 68 may be utilized to apply a plurality of bonding pads 36 to the wound site. As shown, the member 68 carries a pair of transversely spaced bonding pads 36, each pad underlying a pair of adhesive vents 34 for application of the flowable adhesive.

For certain applications, it is believed desirable to provide additional strength or stiffness to the bonding pad. One such manner of doing so is illustrated in FIG. 13. In this arrangement, the bonding pad is made in the form of an envelope 72 of flexible porous material. A semi-flexible or rigid reinforcing member 74 is placed within the bonding pad formed by the envelope 72. The member 74 is provided with openings so that adhesive can pass through the member 74 and wet both the upper and lower layers of the envelope 72.

Figure 14:
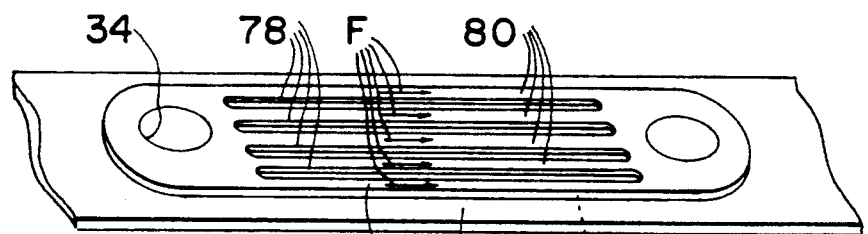
FIG. 14 is a partial perspective view of a carrier member having capillary ducts for enhancing the flow of adhesive.

In order to provide for more complete wetting out of the bonding pad 36, especially when the pad 36 is relatively long, it is desirable to provide flow passages in the carrier member 32 to enhance longitudinal flow of the adhesive. One arrangement for accomplishing this result is illustrated in FIG. 14. In this embodiment, the carrier member 32 has a raised portion 76 overlying the bonding pad 36. A plurality of inverted, longitudinally extending ribs 78 are formed in the carrier member 32, these ribs form a plurality of substantially parallel and longitudinally extending channels 80 for effecting longitudinal flow of the adhesive in the direction of the arrows F at the interface between the bonding pad and the carrier member. By appropriately sizing the cross section of the channels 80, such flow can be effected by capillary action of the adhesive along the channels 80. Thus, the flowable adhesive introduced to the vent 34 will flow longitudinally along substantially the entire length of the bonding pad 36.

Figure 15:
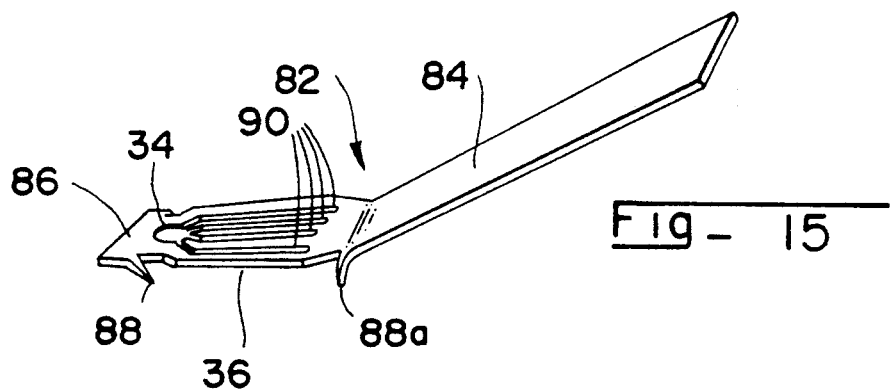
FIG. 15 is a perspective view of another embodiment of wound closure device having a rigid skin engaging member for apposing the wound and placing a bonding pad at the wound site.
Figure 15A:
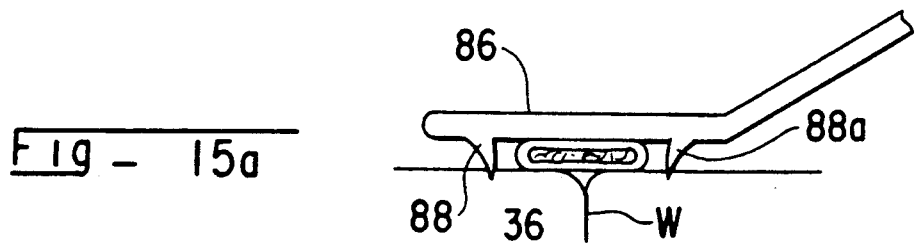
FIG. 15a is a fragmentary side view showing the embodiment of FIG. 15 in wound apposing position.

Referring to FIGS. 15 and 15a, another embodiment of wound closure device in accordance with the invention is illustrated. In this embodiment, a rigid applicator 82, which may be die cut from a strip of metal, includes a handle portion 84 and a bonding pad retaining portion 86, angular disposed with respect to handle 84. The pad retaining portion 86 includes downwardly directed, sharp pointed tangs 88 for engaging the skin of the patient. A bonding pad 36 is releasably secured on the underside of the portion 86 and underlies a vent 34 extending through the portion 86. The portion 86 can also include a plurality of longitudinally extending channels 90, similar in form to those described above in connection with FIG. 14, for aiding in distribution of the adhesive into the pad 36. In use, a tang or tangs 88 at one end of the portion 86 are engaged with the skin of the patient and the wound is apposed by pulling one margin of the wound W toward the other. When the wound margins are so apposed, the opposed set of tangs 88 are pressed into the skin of the patient thereby holding the wound in apposition. While in this position, the flowable adhesive is applied through the vent 34 to the bonding pad 36 and the applicator 82 is retained in place for a time sufficient to allow bonding of the pad 36 to the skin of the patient. Thereafter, the applicator 82 is removed, and the bonding pad 36 remains in place over the wound as a result of the adhesion of the bonding pad to the applicator 82 being designed to be substantially less than the bond strength achieved by the flowable cyanoacrylate adhesive with the skin.

Figure 16:
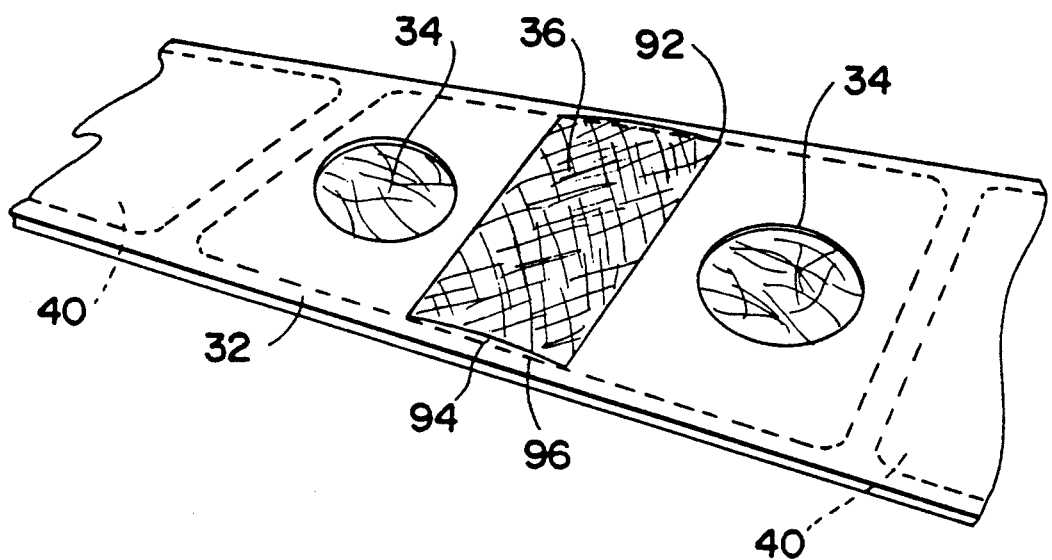
FIG. 16 is a partial perspective view of one manner of releasably mounting a bonding pad to a carrier member.
Figure 17:
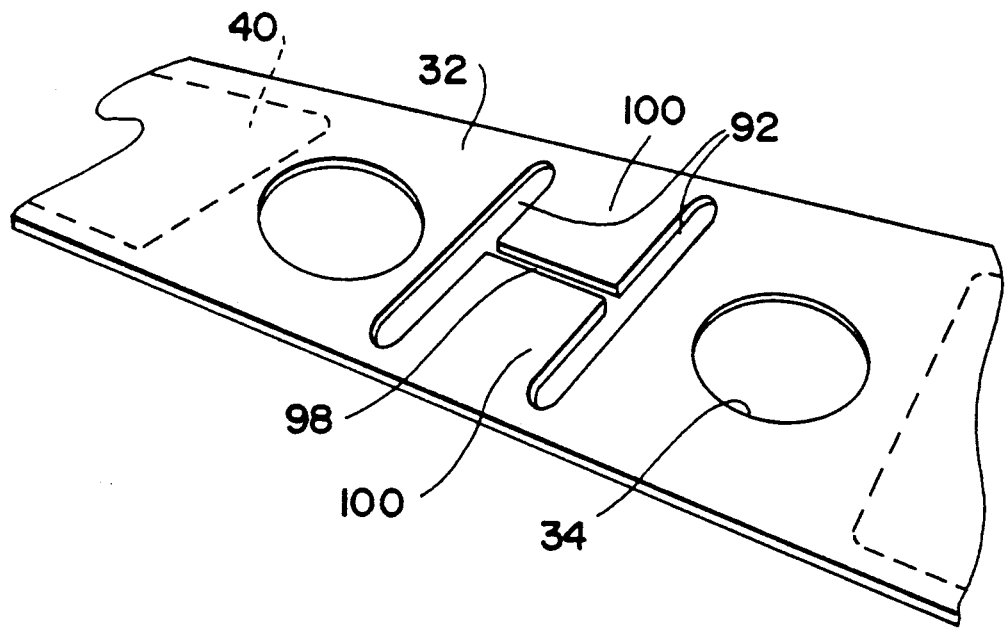
FIG. 17 is a partial perspective view of a carrier member, without a bonding pad, showing an arrangement for releasably mounting a bonding pad on a carrier member.

FIGS. 16 and 17 illustrate additional ways of providing for releasably attachment of the bonding pad to the carrier. As shown in FIG. 16, the carrier member 32 carries a bonding pad 36 and has areas of contact adhesive 40 disposed on the underside of the carrier member 32. The carrier member 32 includes a pair of openings 34 forming ports for the application of the adhesive to the bonding pad 36. The member 32 includes a pair of generally parallel, transversely extending slits 92 formed in the carrier member. One end of the bonding pad 36 is located beneath one of the ports 34 and the opposite end of the bonding pad is located beneath the other of the ports 34. An intermediate portion of the bonding pad extends between the slits 92 and is disposed on the upper side of the carrier member 32. The carrier member 32, which can be in the form of a plastic film, includes a perforated or weakened zone 96 extending between respective ends of the slits 92. In this arrangement, when the bonding pad 36 is adhered to the skin of the patient, removal of the carrier member 32 results in tearing of the carrier member along the weakened zones 96, thereby allowing removal of the carrier member 32. As illustrated in FIG. 17, a similar result can be achieved by use of a longitudinally extending slit 98 which joins the transverse slits 92 thereby forming two facing flaps 100. When the carrier strip 32 is removed, the flaps 90 can flex from beneath the adhered bonding pad, thereby allowing removal of the carrier member 32. An advantage of these arrangements is that the portion of the carrier member located between slits 92 is positioned directly over the wound and can help prevent ingress of liquid adhesive into the wound.

Figure 18:
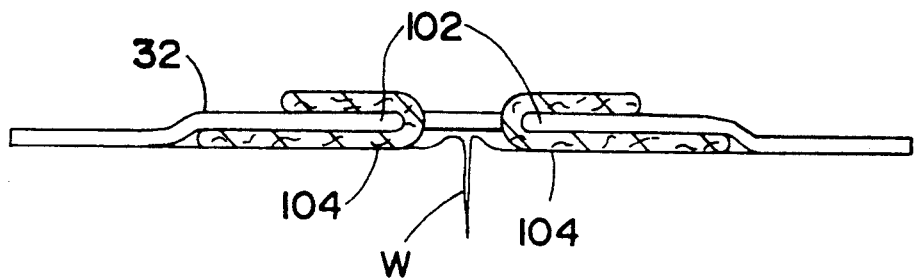
FIG. 18 is a sectional side view of another embodiment of wound closure device having a pair of longitudinally extending flaps about which bonding pads are folded.

Another embodiment of wound closure device in accordance with the invention is shown in FIG. 18. In this embodiment, a pair of oppositely facing longitudinally extending flaps 102 are formed in the carrier member 32. Each of a pair of bonding pads 104 is folded over one of the flaps 102, resulting in a portion of each bonding pad 104 being disposed on a top side of the carrier member 32 and a portion on the bottom side of the carrier member 32. The flowable adhesive is applied to the portions of the pads 104 on the top side of the carrier member 32 and by capillary action and/or perforations in the flaps 102, the portions of the bonding pads in contact with the patient's skin are wetted with the adhesive. In this arrangement, the entire wound closure device remains in place on the patient during the wound healing process. An advantage of this design is that the adhesive is maintained in spaced relation to the wound W, thereby reducing the chance of the adhesive flowing into the wound.

Figure 19:
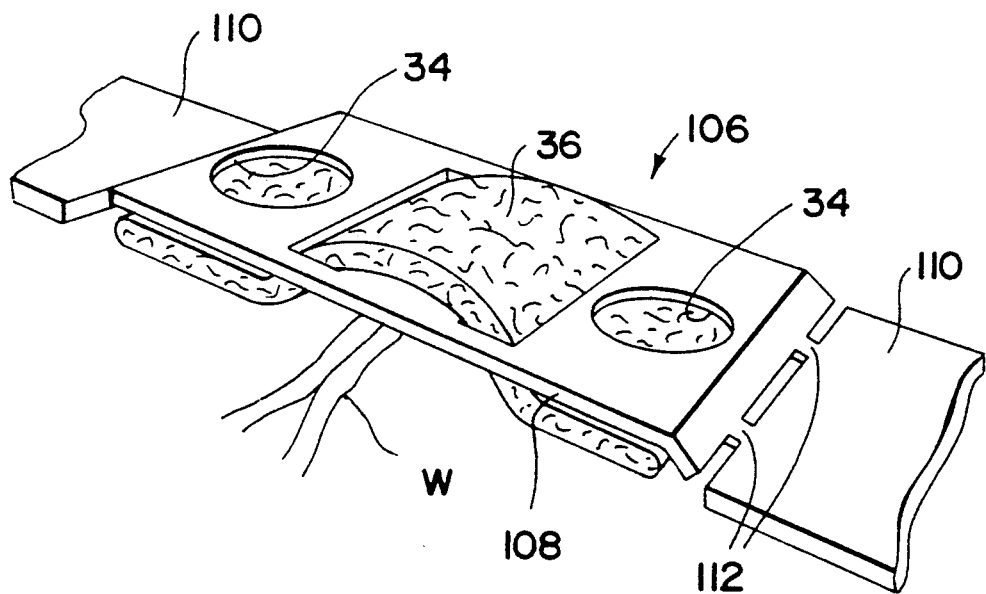
FIG. 19 is a partial perspective view of another embodiment of wound closure device having a rigid or semirigid carrier member with weakened sections for removal of portions of the carrier member.

FIG. 19 shows an embodiment wherein a portion of the carrier member is retained with the bonding pad. In this arrangement, the carrier member 106, preferably formed of a rigid or semi-rigid material, includes a central portion 108 which carries the bonding pad 36. In this arrangement, the intermediate or positioning portions 110 are utilized during the application phase to appose the wound edges and hold the bonding pad in place until the adhesive applied to the bonding pad 36 has set. In order to facilitate removal of unneeded portions of the carrier member 106 after the adhesive has set, the carrier member is slotted or perforated so that only small webs 112 join the central section 108 to the positioning portions 110. In this manner, the portions 110 can be easily removed from the central portion 108, which is held on the patient by the adhered bonding pad 36.

Figure 20:
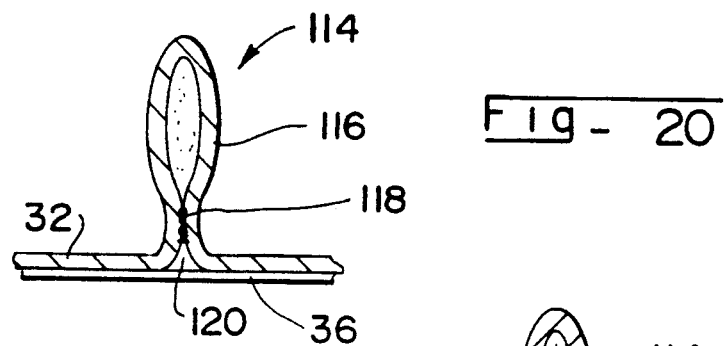
FIG. 20 is a fragmentary sectional view of a wound closure device in accordance with the invention having an adhesive reservoir formed integrally with the carrier member.
Figure 21:
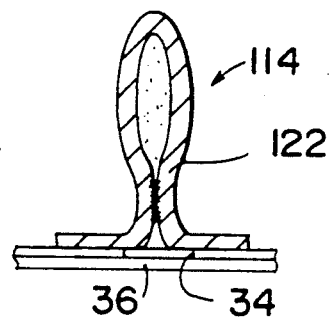
FIG. 21 is a fragmentary cross sectional view of another form of adhesive reservoir fixed to a carrier member.

In the foregoing embodiments, the application of a flowable high strength adhesive was generally considered to be from a separate container of adhesive, such as tube 146 shown in FIG. 1. It is also possible to include a supply of flowable, high strength adhesive with each wound closure device. This feature is illustrated in FIGS. 20, 21, 22 and 22a. FIG. 20 illustrates one manner of integrating a reservoir for the supply of adhesive into the carrier member. In this arrangement, a fold 116 of the material forming carrier member 32 is formed for containing the adhesive. Side edges of the strip of material are joined, for example by heat sealing if the material forming the carrier member 32 is a thermoplastic. The formation of a fold in this manner results in a port 120 which is in fluid communication with the bonding pad 36. A rupturable seal, such as a heat seal 118 is formed between the portions of the fold. By squeezing the fold together, the adhesive is pressurized and ruptures the seal 118, thereby causing the adhesive to flow through port 120 to the bonding pad 36. As shown in FIG. 21, a similar arrangement can be achieved by a separately formed reservoir 122, which can be mounted on the carrier member 32, for example by heat sealing. Liquid adhesive in the reservoir 122 is supplied by rupture of a seal, as described above, to deliver the adhesive to the port 34, thereby wetting the bonding pad 36. In the above-described arrangements incorporating an adhesive supply, as well as those subsequently described, the materials or films from which the adhesive reservoir is formed should include a moisture barrier layer, such as a metallic foil, laminated into the film, to maintain the shelf life of moisture sensitive adhesives, such as cyanoacrylates.

Figure 22:
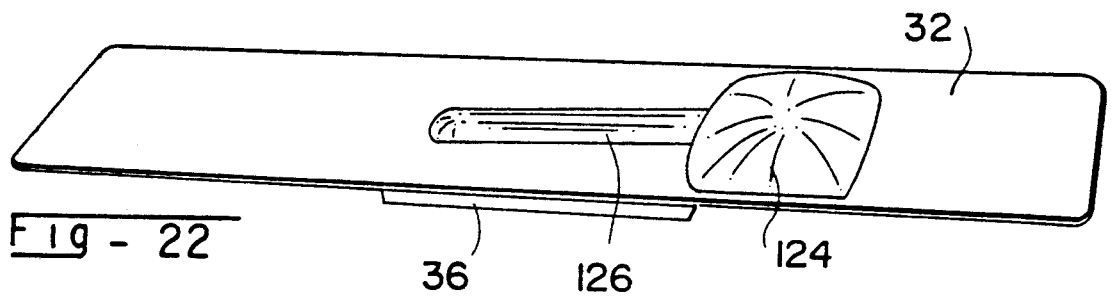
FIG. 22 is a perspective view of a wound closure device showing another arrangement for adhesive supply to the bonding pad.
Figure 22A:
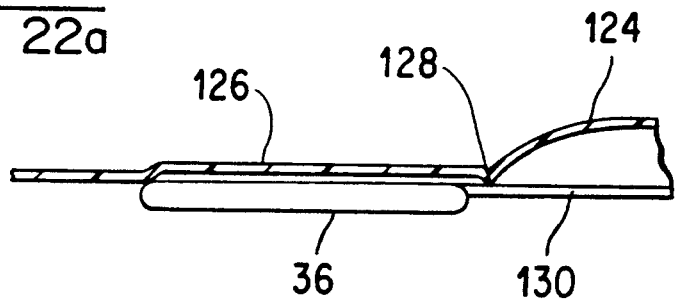
FIG. 22a is a partial cross sectional view of the adhesive supply arrangement shown in FIG. 22.

As shown in FIGS. 22 and 22a, a quantity of adhesive can be held in a bubble 124, formed in the carrier member 32. A longitudinally extending channel 126 is also formed in the carrier member 32 for distributing the adhesive longitudinally along the bonding pad 36. The bubble 124 and channel 126 can be formed by suitable means, such as thermoforming, as part of the carrier member 32. In this arrangement, a barrier or sealing layer 130, such as a foil, is heat sealed about the edges of the bubble 124 to contain the adhesive. The seal at the region 128 between the bubble 124 and the channel 126 is rupturable so that, upon application of force to the bubble 124, the liquid adhesive is placed under pressure and ruptures the seal 128, thereby allowing the adhesive to flow in the channel 126.

FIG. 23 also illustrates a wound closure member having a supply of flowable adhesive. In this arrangement, a bubble 132 is formed in the carrier member 32 and contains a supply of adhesive 134. A layer of adhesive impervious material 136, such as a foil, is adhered to the underside of the carrier member 32 to contain the adhesive within the bubble 132. A central portion of the bubble 132 includes a pointed portion 138. When the central portion of bubble 132 is depressed, the pointed portion 138 ruptures the foil 136, thereby allowing the adhesive to flow into the bonding pad 36.

Figure 25:
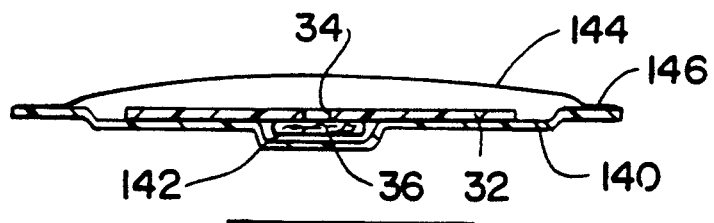
FIG. 25 is a cross sectional view of the arrangement shown in FIG. 24 with a sterility barrier film applied thereto.

In order to speed the application of the wound closure members to the patient, it is believed desirable to apply the adhesive to the bonding pad prior to application of the wound closure device to the patient. An arrangement for implementing this mode of application is illustrated in FIGS. 24 and 25. A shown, a plurality of wound closure devices 132 are disposed in a tray 140 having a central recess 142, wherein the bonding pad 36 is spaced from the tray. In this arrangement, the adhesive can be applied, for example via the port 34 to the bonding pad while it is in the tray and then closure member is thereafter applied to the patient. Another advantage of this design is that the tray 140 can be utilized as a part of a sterility barrier package to which a protective cover sheet 144 is applied. In such an arrangement, the tray 140 is formed by suitable means, such as thermoforming, from a semi-rigid or rigid plastic barrier material. The coversheet 144 can be a microbe impervious, gas pervious material, if gas sterilization is used, or can be a suitable impervious material if other sterilization methods, such as in radiation, are utilized.

If desired, the tray 140 can include a well 162 sized to contain the tube 164 of flowable adhesive. In this arrangement, the wound apposition devices and the supply of adhesive can be delivered to the surgical field in sterile condition.

In use, the coversheet 144 is heat sealed to the tray 140 at the peripheral heat seal surfaces 146 in a manner such that the sheet 144 can be peeled away from the tray 140. If desirable, the package unit comprising the tray 140 and cover 144 can be placed within an additional sterility barrier so that the tray 140 can be introduced to the surgical field in a sterile condition. Any of the embodiments of wound closure device disclosed may be packaged in similar fashion and using known means to provide the devices and adhesive containers in sterile condition.

Figure 26:
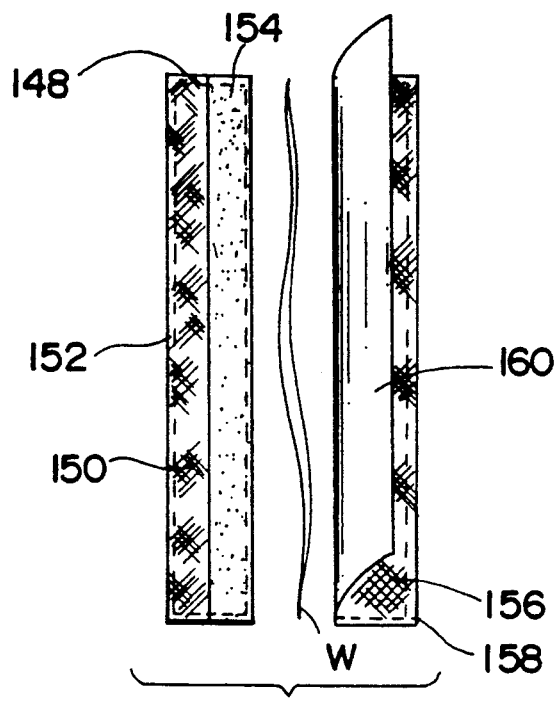
FIG. 26 is another embodiment of wound closure device in accordance with the invention.

In FIG. 26, another embodiment of wound closure device incorporating the invention is illustrated. In this arrangement, a first strip 148 having a porous portion 150 formed of a mesh or similar material has a skin contact adhesive applied on one surface thereof. As is conventional, a protective release layer can be applied over the contact adhesive. The first strip 148 also includes a second portion 154 on the side opposite the patient contact side, to which is applied a contact adhesive. The portion 154 is also covered by a protective release layer (not shown). The wound closure device also includes a second strip of material 156 formed of a porous mesh material. Strip 156 also includes a contact adhesive 158 protected by a release layer (not shown). The sheet 156 includes a flexible wound apposing sheet fixed to the strip 156. In use, the first strip 148 is positioned along one margin of the wound by use of the contact adhesive 152. Long term fixation of the strip 148 is achieved by applying the flowable adhesive onto the porous portion 150. In a similar fashion, the second strip 156 is applied to the opposite margin of the wound W and the flowable adhesive applied. After suitable bond strength is achieved, the contact adhesive 154 on strip 148 is revealed by removal of the above-mentioned protective layer. The wound opposing film or sheet 120 is then drawn across the wound and adhered to the contact adhesive 154 as well as any unset adhesive disposed on the mesh 150. An advantage of this embodiment is that the sheet 160 covers and protects the wound W.

From the foregoing, it can be seen that an improved means and method for wound closure, particularly skin closure, is achieved by the disclosed invention. Wound apposition is accomplished initially by means of a member extending across the wound and longer term, more permanent apposition is achieved by application of a flowable adhesive to a porous bonding member. The bonding member remains in place for a sufficient period of time to allow substantial healing of the wound. Removal of the closure device can occur as a result of the normal body process of reepithelialization of the skin, thereby avoiding the need for removal procedures that can be painful and risk wound infection.

What is claimed is:

1. A wound closure system comprising:
   a porous bonding member;
   means for affixing the porous bonding member in a wound apposing position on the skin of a patient; and
   a source of flowable adhesive and a means for delivering the flowable adhesive to the bonding member, whereby, upon application of the adhesive to the bonding member, the adhesive flows through the bonding member and adheres the porous member to the skin of the patient.

2. The wound closure system of claim 1, wherein the adhesive source of flowable comprises a container having a cyanoacrylate adhesive contained therein.

3. A wound closure system as in claim 1, further comprising a sterility barrier package, said bonding member and said positioning means being in a sterile condition within said barrier package.

4. A wound closure system as in claim 3, wherein the adhesive delivery means is disposed within said barrier package.

5. A wound closure system comprising:
   a carrier member;
   means on the carrier member for holding edges of a wound of a patient in apposed condition;
   a porous wound apposing member for receiving a flowable adhesive;
   means for mounting the wound apposing member on the carrier member; and
   a source of flowable adhesive and a means for delivering the flowable adhesive to the porous wound apposing member.

6. A wound closure system as in claim 5, wherein the carrier member is formed of a flexible sheet material.

7. A wound closure system as in claim 6, further comprising an aperture in the carrier member, said wound apposing member being located on one side of the carrier member and overlying said aperture.

8. A wound closure system as in claim 6, wherein the means on the carrier member for holding the wound in apposed condition comprises a contact adhesive.

9. A wound closure system as in claim 6, wherein the means for mounting the porous wound apposing member on the carrier member comprises means for readily releasably securing the porous wound apposing member on the carrier member.

10. A wound closure system as in claim 5, wherein the porous wound apposing member is a body formed of fibrous material.

11. A wound closure system as in claim 5, further comprising a liquid impervious membrane, said membrane being positioned to cover at least a portion of a patient contact surface of the wound apposing member.

12. A wound closure system comprising:
an elongate carrier member;
an adhesive delivery port formed in the carrier member;
a porous wound apposing bonding pad;
means mounting the bonding pad on the carrier member adjacent the adhesive delivery port;
means for affixing the carrier member on a patient; and
a source of flowable adhesive and a means for delivering the flowable adhesive to the adhesive delivery port.

13. A wound closure system as in claim 12, wherein the affixing means is a contact adhesive.

14. A wound closure system as in claim 12, wherein the adhesive delivery port comprises a first opening in the carrier member and a second opening in the carrier member spaced longitudinally from the first opening, said bonding pad being located adjacent said first and second openings.

15. A wound closure system as in claim 13, further comprising a removable protective strip overlying the contact adhesive.

16. A wound closure system as in claim 12, wherein the bonding pad is releasably secured on the carrier member.

17. A wound closure system as in claim 12, further comprising an anti-backflow membrane disposed between the carrier member and the bonding pad.

18. A wound closure system as in claim 17, wherein the anti-backflow membrane comprises a perforated sheet.

19. A wound closure system as in claim 12, further comprising a screen member overlying the bonding pad.

20. A wound closure system as in claim 19, wherein the screen member comprises a perforated sheet bonded to the carrier member.

21. A wound closure system as in claim 12, wherein the carrier member includes perforations therein positioned outwardly of the location of the bonding pad.

22. A wound closure system as in claim 12, further comprising an adhesive impervious barrier member disposed over a portion of a patient contact surface of the bonding pad.

23. A wound closure system as in claim 12, wherein the carrier comprises a strip having a raised portion and the bonding pad is positioned on the carrier member at the raised portion.

24. A wound closure system as in claim 12, wherein the carrier member includes a grasping area at one end thereof free of means for affixing the carrier member on a patient.

25. A wound closure system as in claim 12, wherein a plurality of bonding pads are mounted on the carrier member.

26. A wound closure system as in claim 25, wherein the bonding pads are disposed transversely on the carrier member.

27. A wound closure system as in claim 12, further comprising capillary ducts located at an interface between the carrier member and the bonding pad.

28. A wound closure system as in claim 27, wherein the capillary ducts are formed in the carrier member.

29. A wound closure system as in claim 12, wherein the carrier member is a strip having a first side, adapted to be placed in contact with a patient, and a second side opposed to the first side; and the bonding pad has a first end portion disposed on the first side of the carrier member, an intermediate portion disposed on the second side of the carrier member, and a second end portion disposed on the first side of the carrier member.

30. A wound closure system as in claim 29, wherein the carrier member includes a pair of spaced openings and the intermediate portion of the bonding pad extends between said openings.

31. A wound closure system as in claim 30, wherein the bonding pad is secured to portions of the carrier member disposed between the openings and the carrier member includes a weakened separation portion extending between the openings.

32. A wound closure system as in claim 30, further comprising a slit in the carrier member extending substantially longitudinally between the openings.

33. A wound closure system as in claim 12, wherein the carrier member includes a transversely extending weakened portion adjacent each end of the bonding pad, for permitting ready removal of ends of the carrier member.

34. A wound closure system as in claim 12, wherein the adhesive is a cyanoacrylate.

35. A wound closure system as in claim 12, wherein the a source of flowable adhesive comprises an adhesive container, means mounting the adhesive container on the carrier member, a supply of flowable adhesive in the container and means for providing fluid communication between the container and the bonding pad.

36. A wound closure system as in claim 34, wherein the container comprises a flexible film and a pressure rupturable closure for maintaining the adhesive within the container.

37. A wound closure system as in claim 35, wherein the container is integrally formed in a portion of the carrier member.

38. A wound closure system comprising:
a porous bonding pad;
a contact adhesive on one surface of the bonding pad for maintaining the bonding pad in wound apposing position on a patient; and
a flowable adhesive for application to the bonding pad for securing the bonding pad on a patient.

39. A wound closure system as in claim 38, wherein the bonding pad includes means on a second surface thereof, opposite the first surface, for indicating a location for applying the flowable adhesive to the bonding pad.

40. A wound closure system as in claim 38, further comprising a removable protective means disposed over the contact adhesive.

41. A method of wound apposition comprising:

placing an elongate member in engagement with a first wound margin;

holding the wound in apposition by drawing the member across the wound and engaging an opposed wound margin;

placing a porous bonding member at apposed wound margins with a first portion thereof disposed at a first wound margin and a second portion thereof disposed at a second wound margin; and applying a flowable adhesive to the first and second portions of the bonding member and allowing the adhesive to adhere the bonding member to the respective wound margins.

42. A wound closure method as in claim 41, further comprising the step of removing the elongate member from the wound after the bonding member is adhered to the wound margins.

43. A wound closure method as in claim 41, wherein the elongate member and the bonding pad are simultaneously applied to the wound.

44. A wound closure method as in claim 41, wherein the adhesive comprises a cyanoacrylate.

45. A method of wound apposition comprising:
placing a first part of an elongate member in engagement with a first wound margin;

holding the wound in apposition by placing a second part of the elongate member in engagement with a second wound margin opposed to the first wound margin;

placing a porous bonding member at opposed wound margins with a first portion thereof disposed at the first wound margin and a second portion thereof disposed at the second wound margin; and applying a flowable adhesive to the first and second portions of the porous bonding member and allowing the adhesive to adhere the porous bonding member to the respective wound margins.

46. A wound closure method as in claim 45, further comprising the step of removing the elongate member from the wound after the bonding member is adhered to the wound margins.

47. A wound closure method as in claim 45, wherein the elongate member and the porous bonding pad are simultaneously applied to the wound.

48. A wound closure method as in claim 45, wherein the adhesive comprises a cyanoacrylate.

49. A wound closure method as in claim 45, wherein the first and second wound margins comprise the skin of a patient.

50. A wound closure method as in claim 41, wherein the first and second wound margins comprise the skin of a patient.

51. A method of closing a wound comprising the steps of:
placing a porous bonding member at a wound site with a first part of the bonding member disposed on a first portion of tissue at the wound site and a second part of the bonding member disposed on a second portion of tissue at the wound site to be apposed with the first portion of tissue; and applying a flowable adhesive to the first and second parts of the porous bonding member and allowing the adhesive to flow into the porous bonding member and adhere the porous bonding member to the first and second portions of tissue.

52. A method of closing a wound as in claim 51, further comprising the step of maintaining the first and second tissue portions apposed while the adhesive adheres the bonding member to said tissue portions.

53. A method of closing a wound as in claim 51, wherein the flowable adhesive is a cyanoacrylate.

54. A method of closing a wound as in claim 53, wherein the first and second portions of tissue comprise the skin of a patient.

55. A wound closure system as in claim 5, wherein the means on the carrier member for holding the edges of the wound in apposed condition comprises a contact adhesive.

56. A wound closure system as in claim 5, wherein the porous wound apposing member is a body formed of fibrous material.

57. A wound closure system as in claim 35, wherein the adhesive container comprises a pierceable layer and means for piercing the pierceable layer.

* * * * *

UNITED STATES PATENT AND TRADEMARK OFFICE
CERTIFICATE OF CORRECTION

PATENT NO. : 5,259,835
DATED : November 9, 1993
INVENTOR(S) : Jeffrey G. CLARK; Douglas M. SPRANGER; Paul J. MULHAUSER and Paul R. LACOTTA It is certified that error appears in the above-indentified patent and that said Letters Patent is hereby corrected as shown below:

Column 10, line 43, after "flowable" insert --adhesive--;
line 49, after "the" insert --source of flowable--;
line 50, delete "delivery means".

Signed and Sealed this

Thirteenth Day of September, 1994

Attest:

BRUCE LEHMAN

Attesting Officer        Commissioner of Patents and Trademarks